United States Patent
Hogendijk et al.

(10) Patent No.: US 7,862,608 B2
(45) Date of Patent: Jan. 4, 2011

(54) VASCULAR PROSTHESIS AND METHODS OF USE

(75) Inventors: Michael Hogendijk, Palo Alto, CA (US); Todd Thompson, San Jose, CA (US)

(73) Assignee: NovoStent Corporation, Mountain View, CA (US)

( * ) Notice: Subject to any disclaimer, the term of this patent is extended or adjusted under 35 U.S.C. 154(b) by 937 days.

(21) Appl. No.: 10/746,668

(22) Filed: Dec. 23, 2003

(65) Prior Publication Data

US 2004/0186556 A1  Sep. 23, 2004

Related U.S. Application Data

(63) Continuation-in-part of application No. 10/723,565, filed on Nov. 25, 2003, now abandoned, which is a continuation-in-part of application No. 10/342,427, filed on Jan. 13, 2003.

(60) Provisional application No. 60/436,516, filed on Dec. 24, 2002.

(51) Int. Cl.
*A61F 2/06* (2006.01)
*A61M 29/00* (2006.01)

(52) U.S. Cl. .............. 623/1.22; 623/1.15; 623/1.16; 623/1.31; 623/1.51; 606/108; 606/194; 606/195; 606/198

(58) Field of Classification Search .............. 623/1.15, 623/1.16, 1.22, 1.51, 1.53, 1.54; 606/194, 606/195, 198
See application file for complete search history.

(56) References Cited

U.S. PATENT DOCUMENTS

| 4,553,545 | A |   | 11/1985 | Maass et al. |
| 4,655,771 | A |   | 4/1987 | Wallsten |
| 4,665,918 | A |   | 5/1987 | Garza et al. |
| 4,739,762 | A |   | 4/1988 | Palmaz |
| 4,760,849 | A |   | 8/1988 | Kropf |
| 4,768,507 | A |   | 9/1988 | Fischell et al. |
| 4,800,882 | A | * | 1/1989 | Gianturco .......... 606/194 |
| 4,886,062 | A |   | 12/1989 | Wiktor |

(Continued)

FOREIGN PATENT DOCUMENTS

EP  1 110 515 A2  6/2001

(Continued)

OTHER PUBLICATIONS

Final Office Action mailed Aug. 8, 2008 for U.S. Appl. No. 10/342,427; filed Jan. 13, 2003.

(Continued)

*Primary Examiner*—Vy Q Bui
(74) *Attorney, Agent, or Firm*—James F. Hann; Haynes Beffel & Wolfeld, LLP

(57) ABSTRACT

The present invention is directed to an implantable vascular prosthesis configured for use in a wide range of applications, such as treating aneurysms, maintaining patency in a vessel, and allowing for the controlled delivery of therapeutic agents to a vessel wall. The prosthesis comprises one or more helical sections coupled to one or more anchoring sections having a generally zig-zag or cell-like configuration. The prosthesis is configured to conform to a vessel wall without substantially remodeling the vessel, and further is configured to be precisely deployed in a vessel without shifting or foreshortening during deployment.

17 Claims, 11 Drawing Sheets

U.S. PATENT DOCUMENTS

| | | | |
|---|---|---|---|
| 4,969,458 A | | 11/1990 | Wiktor |
| 5,019,090 A | | 5/1991 | Pinchuk |
| 5,041,126 A | | 8/1991 | Gianturco |
| 5,104,404 A | | 4/1992 | Wolff |
| 5,147,370 A | | 9/1992 | McNamara et al. |
| 5,246,445 A | | 9/1993 | Yachia et al. |
| 5,314,444 A | | 5/1994 | Gianturco |
| 5,342,387 A | | 8/1994 | Summers |
| 5,344,426 A | | 9/1994 | Lau et al. |
| 5,383,892 A | | 1/1995 | Cardon et al. |
| 5,421,955 A | | 6/1995 | Lau et al. |
| 5,423,885 A | | 6/1995 | Williams |
| 5,441,515 A | | 8/1995 | Khosravi et al. |
| 5,443,500 A | | 8/1995 | Sigwart |
| 5,476,505 A | | 12/1995 | Limon |
| 5,540,713 A | | 7/1996 | Schnepp-Pesch et al. |
| 5,551,954 A | | 9/1996 | Buscemi et al. |
| 5,556,413 A | | 9/1996 | Lam |
| 5,575,818 A | * | 11/1996 | Pinchuk .................. 623/1.15 |
| 5,603,722 A | | 2/1997 | Phan et al. |
| 5,607,445 A | | 3/1997 | Summers |
| 5,607,478 A | | 3/1997 | Lentz et al. |
| 5,632,771 A | | 5/1997 | Boatman et al. |
| 5,716,396 A | | 2/1998 | Williams, Jr. |
| 5,741,333 A | * | 4/1998 | Frid ............................ 623/1.2 |
| 5,817,126 A | * | 10/1998 | Imran ........................ 623/1.15 |
| 5,817,152 A | | 10/1998 | Birdsall et al. |
| 5,824,052 A | | 10/1998 | Khosravi et al. |
| 5,824,053 A | | 10/1998 | Khosravi et al. |
| 5,830,179 A | | 11/1998 | Mikus et al. |
| 5,833,699 A | | 11/1998 | Chuter |
| 5,876,432 A | | 3/1999 | Lau et al. |
| 5,954,744 A | | 9/1999 | Phan et al. |
| 6,027,526 A | | 2/2000 | Limon et al. |
| 6,080,191 A | | 6/2000 | Summers |
| 6,086,604 A | | 7/2000 | Fischell et al. |
| 6,156,062 A | | 12/2000 | McGuinness |
| 6,238,430 B1 | | 5/2001 | Klumb et al. |
| 6,248,122 B1 | | 6/2001 | Klumb et al. |
| 6,331,189 B1 | | 12/2001 | Wolinsky et al. |
| 6,334,870 B1 | | 1/2002 | Ehr et al. |
| 6,348,065 B1 | | 2/2002 | Brown et al. |
| 6,409,752 B1 | | 6/2002 | Boatman et al. |
| 6,409,754 B1 | | 6/2002 | Smith et al. |
| 6,416,545 B1 | * | 7/2002 | Mikus et al. ............... 623/1.19 |
| 6,423,091 B1 | | 7/2002 | Hojeibane |
| 6,425,915 B1 | | 7/2002 | Khosravi et al. |
| 6,432,128 B1 | | 8/2002 | Wallace et al. |
| 6,503,270 B1 | | 1/2003 | Richter et al. |
| 6,508,834 B1 | * | 1/2003 | Pinchasik et al. .......... 623/1.16 |
| 6,514,285 B1 | * | 2/2003 | Pinchasik ................. 623/1.22 |
| 6,533,805 B1 | | 3/2003 | Jervis |
| 6,540,775 B1 | | 4/2003 | Fischell et al. |
| 6,565,600 B2 | | 5/2003 | Hojeibane |
| 6,572,643 B1 | | 6/2003 | Gharibadeh |
| 6,576,006 B2 | | 6/2003 | Limon et al. |
| 6,589,276 B2 | | 7/2003 | Pinchasik et al. |
| 6,596,021 B1 | | 7/2003 | Lootz |
| 6,607,554 B2 | | 8/2003 | Dang et al. |
| 6,635,084 B2 | | 10/2003 | Israel et al. |
| 6,645,237 B2 | | 11/2003 | Klumb et al. |
| 6,656,220 B1 | | 12/2003 | Gomez et al. |
| 6,660,032 B2 | | 12/2003 | Klumb et al. |
| 6,679,911 B2 | | 1/2004 | Burgermeister |
| 6,736,844 B1 | | 5/2004 | Glatt et al. |
| 6,746,475 B1 | | 6/2004 | Rivelli, Jr. |
| 7,169,175 B2 | | 1/2007 | Cottone, Jr. et al. |
| 2001/0020182 A1 | | 9/2001 | Klumb et al. |
| 2002/0004676 A1 | | 1/2002 | Wallace et al. |
| 2002/0004679 A1 | | 1/2002 | Eury et al. |
| 2002/0095206 A1 | | 7/2002 | Addonizio et al. |
| 2004/0034402 A1 | | 2/2004 | Bales et al. |
| 2004/0044401 A1 | | 3/2004 | Bales et al. |
| 2004/0073293 A1 | | 4/2004 | Thompson |
| 2004/0122504 A1 | | 6/2004 | Hogendijk |
| 2004/0172123 A1 | | 9/2004 | Lootz et al. |
| 2005/0165469 A1 | | 7/2005 | Hogendijk |
| 2007/0185560 A1 | | 8/2007 | Roeder et al. |

FOREIGN PATENT DOCUMENTS

| | | |
|---|---|---|
| WO | WO 97/21399 A1 | 6/1997 |
| WO | WO 98/38945 A1 | 9/1998 |
| WO | WO0062711 | 10/2000 |

OTHER PUBLICATIONS

Amendment After Final filed on Oct. 8, 2008 in response to Aug. 8, 2008 Final Office Action for U.S. Appl. No. 10/342,427; filed Jan. 13, 2003.

Final Office Action mailed Jun. 25, 2009 for U.S. Appl. No. 11/716,521; filed Mar. 9, 2007, 10 pgs.

Final Office Action mailed Oct. 29, 2009 for U.S. Appl. No. 10/342,427; filed Jan. 13, 2003; 8 pages.

* cited by examiner

VASCULAR PROSTHESIS AND METHODS OF USE

REFERENCE TO RELATED APPLICATIONS

This application is a continuation-in-part of U.S. patent application Ser. No. 10/723,565, filed Nov. 25, 2003, which is a continuation-in-part of U.S. patent application Ser. No. 10/342,427, filed Jan. 13, 2003, which claims priority from U.S. provisional patent application Ser. No. 60/433,065, filed Dec. 24, 2002.

FIELD OF THE INVENTION

The present invention relates to an implantable vascular prosthesis configured for use in a wide range of applications, and more specifically, a ribbon-type prosthesis having a helical section and at least one anchor section.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath, then self-expand when the sheath is retracted. Such stents commonly have several drawbacks, for example, the stents may experience large length changes during expansion (referred to as "foreshortening") and may shift within the vessel prior to engaging the vessel wall, resulting in improper placement. Additionally, many self-expanding stents have relatively large delivery profiles because the configuration of their struts limits further compression of the stent. Accordingly, such stents may not be suitable for use in smaller vessels, such as cerebral vessels and coronary arteries.

Other drawbacks associated with the use of coils or stents in the treatment of aneurysms is that the devices, when deployed, may have a tendency to straighten or otherwise remodel a delicate cerebral vessel, which may cause further adverse consequences. Moreover, such devices may not adequately reduce blood flow from the cerebral vessel into the sac of the aneurysm, which may increase the likelihood of rupture. Generally, if a greater surface area is employed to cover the sac, the delivery profile of the device may be compromised due to the increased surface area, and the device also may be more rigid and cause remodeling of the vessel.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, then constrained within a delivery sheath. The delivery sheath is retracted to expose the distal portion of the stent and anchor the distal end of the stent. As the delivery sheath is further retracted, subsequent individual turns of the stent unwind to conform to the diameter of the vessel wall.

The stent described in the foregoing publication has several drawbacks. For example, due to friction between the turns and the sheath, the individual turns of the stent may bunch up, or overlap with one another, when the delivery sheath is retracted. In addition, once the sheath is fully retracted, the turns may shift within the vessel prior to engaging the vessel wall, resulting in improper placement of the stent. Moreover, because the distal portion of the stent may provide insufficient engagement with the vessel wall during subsequent retraction of the remainder of the sheath, ambiguity concerning accuracy of the stent placement may arise.

When utilizing stents in interventional procedures, it may be advantageous to deliver therapeutic agents to a vessel wall via the surface of the stent. Drug eluting stents have many advantages, such as controlled delivery of therapeutic agents over an extended period of time without the need for intervention, and reduced rates of restenosis after angioplasty procedures. Typically, the drug is disposed in the matrix of a bioabsorbable polymer coated on an exterior surface of the struts of the stents, and then gradually released into a vessel wall. The quantity of the therapeutic agent provided by the stent generally is limited by the surface area of the struts. Increasing the surface area of the struts may enhance drug delivery capability, but may compromise the overall delivery profile of the stent. There therefore exists a need for a prosthesis having a reduced delivery profile and enhanced drug delivery capabilities.

In view of these drawbacks of previously known devices, it would be desirable to provide apparatus and methods for an implantable vascular prosthesis comprising one or more ribbon-type stent bodies joined by one or more radially expanding anchors, wherein the prosthesis is configured to be used in a wide range of applications including, but not limited to, treating aneurysms, maintaining patency in a vessel, and delivering drugs to a vessel.

It also would be desirable to provide apparatus and methods for a vascular prosthesis comprising a ribbon-type stent having a torsional stabilizer that enhances frictional engagement with the vessel.

It also would be desirable to provide apparatus and methods for a vascular prosthesis that is flexible enough to conform to a natural shape of a vessel without substantially remodeling the vessel.

It further would be desirable to provide apparatus and methods for a vascular prosthesis having radially expanding anchors that allow for controlled deployment of a ribbon-type stent at a desired location within a vessel.

It still further would be desirable to provide apparatus and methods for a vascular prosthesis that has a surface area that may be selected to facilitate in-vivo delivery of therapeutic agents without adversely impacting the mechanical properties (e.g., radial strength, flexibility, etc.) of the stent.

It yet further would be desirable to provide apparatus and methods for a vascular prosthesis that has a substantially small delivery configuration to allow the prosthesis to be used in smaller vessels.

SUMMARY OF THE INVENTION

In view of the foregoing, it is an object of the present invention to provide apparatus and methods for an implantable vascular prosthesis comprising one or more ribbon-type stent bodies joined by one or more radially expanding anchors, wherein the prosthesis is configured to be used in a wide range of applications including, but not limited to, treating aneurysms, maintaining patency in a vessel, and delivering drugs to a vessel.

It is also an object of the present invention to provide apparatus and methods for a vascular prosthesis comprising a ribbon-type stent having a torsional stabilizer that provides frictional engagement with the vessel wall.

It is a further object of the present invention to provide apparatus and methods for a vascular prosthesis that is flexible enough to conform to a natural shape of a vessel without substantially remodeling the vessel.

It is another object of the present invention to provide apparatus and methods for a vascular prosthesis having radially expanding anchors that allow for controlled deployment of a ribbon-type stent at a desired location within a vessel.

It is a further object of the present invention to provide apparatus and methods for a vascular prosthesis that has a surface area that may be selected to facilitate in-vivo delivery of therapeutic agents.

It is a further object of the present invention to provide apparatus and methods for a vascular prosthesis that has a-substantially small delivery configuration to allow the prosthesis to be used in smaller vessels.

These and other objects of the present invention are accomplished by providing a vascular prosthesis comprising one or more ribbon-type stent bodies joined by one or more radially expanding anchors, wherein the prosthesis is configured to engage a vessel wall and adapt to a natural curvature of the vessel wall. The vascular prosthesis may be used in a wide range of applications, such as treating aneurysms, maintaining patency in a vessel, e.g., after an angioplasty procedure, and other procedures requiring a controlled delivery of therapeutic drugs to a vessel.

In a preferred embodiment, the vascular prosthesis comprises a shape memory material, such as Nitinol, and includes a radially expandable distal anchor section having a generally zig-zag or cell-like configuration coupled to one end of a helical section disposed proximal of the distal anchor, the helical section formed of a plurality of mesh turns. According to some embodiments, the vascular prosthesis further comprises a radially expandable proximal anchor section having a generally zig-zag or cell-like configuration coupled to the other end of the helical section. According to other embodiments, the vascular prosthesis comprises a plurality of helical sections interconnected by one or more radially expandable anchors. In yet further alternative embodiments, the distal anchor section is joined to the helical section by a torsional stabilizer that enhances contact and friction with the vessel wall.

The prostheses of the present invention are delivered to a target vessel in a contracted state, constrained within an outer sheath, in which radially inwardly directed compressive forces are applied by the outer sheath to the anchor section(s). In the contracted state, the helical section is wound down to a smaller configuration, so that adjacent turns preferably partially overlap, and are constrained in the contracted state by the outer sheath.

In a preferred method of operation of a prosthesis having both distal and proximal anchor sections, the distal anchor section, helical section and proximal anchor section are provided in their contracted states within an outer sheath and the prosthesis is fluoroscopically advanced into a selected vessel using techniques that are per se known in the art. The helical section then is positioned adjacent a target region of a vessel, such as an aneurysm or a stenosed region, with the distal anchor section positioned distal of the target region. The outer sheath then is retracted proximally to cause the distal anchor section to self-deploy and engage an inner wall of the vessel distal of the target region. A distal portion of the distal anchor section may be biased radially outward, or provided with proximally-directed barbs, to facilitate secure anchoring of the distal anchor section within the vessel.

Once the distal anchor section is securely anchored distal of the target region, the outer sheath further is retracted to cause the helical section to self-deploy and engage the vessel wall at the target region. Advantageously, by providing a distal anchoring element prior to deploying the helical section, each turn of the helical section will unwind in a controlled manner as the outer sheath is retracted. This technique ensures that the prosthesis will not shift within the vessel during deployment. The proximal anchor section, if provided, then is deployed by further retraction of the outer sheath.

The vascular prosthesis of the present invention is flexible enough to conform to the shape of a delicate vessel without substantially remodeling the vessel. In particular, the zig-zag or cell-like configuration of the distal anchor section may conform to a natural curvature of a vessel wall better than traditional stents having interconnected struts, which may be more rigid. Additionally, the mesh configuration of the helical section conforms to vasculature of the target region since each of the plurality of turns is free to assume a curved configuration substantially independently of one another. Also, because the helical section of the vascular prosthesis has a ribbon-like structure, it may be wound down to a contracted state with a substantially reduced delivery profile, compared to slotted-tube stents. This feature makes the stent of the present invention especially useful for treating defects in smaller vessels, such as cerebral arteries.

In accordance with another aspect of the present invention, the plurality of turns may comprise a substantially increased surface area relative to conventional stents that have a plurality of interconnected struts. The increased surface area of the turns is particularly advantageous for localized drug delivery. The turns may be coated with a drug-laden polymer coating or, alternatively, one or more dimples or through-holes may be disposed in a lateral surface of the turns to elute drugs over an extended period of time.

Methods of using the vascular prosthesis of the present invention, for example, in the treatment of an aneurysm, also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to an implantable vascular prosthesis configured for use in a wide range of applications, such as treating aneurysms, maintaining patency in a vessel, and allowing for the controlled delivery of therapeutic agents to a vessel wall. The prosthesis has a ribbon-type configuration that provides a substantially smaller delivery profile than other known devices, while having an increased surface area to allow for delivery of the therapeutic agents. Additionally, the prosthesis is configured to conform to a vessel wall without substantially remodeling the vessel, and further is configured to provide improved accuracy during deployment relative to previously known devices.

Figure 1A:
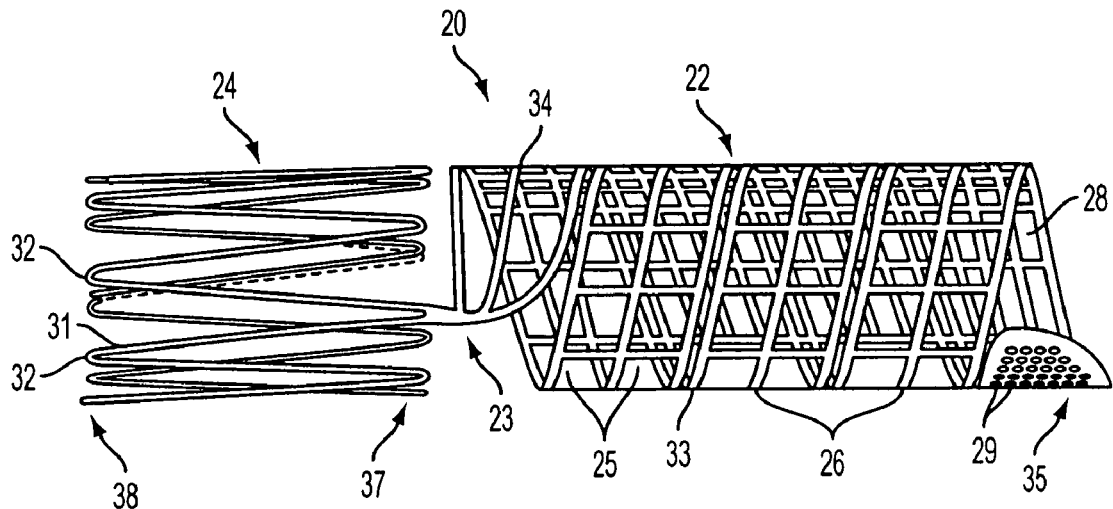
FIGS. 1A-1B are, respectively, side and perspective views of a vascular prosthesis of the present invention.
Figure 1B:
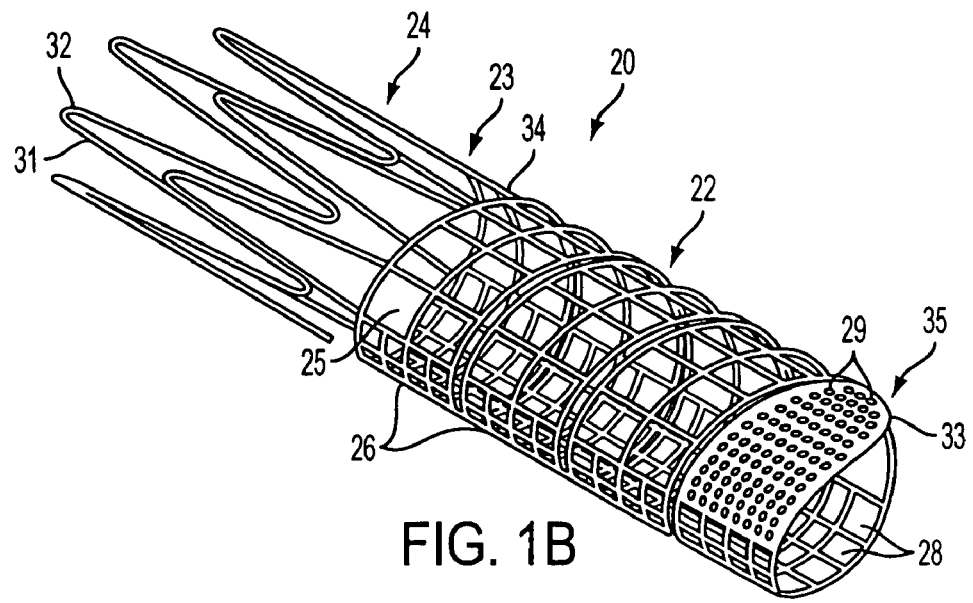

Referring now to FIG. 1, a first embodiment of a vascular prosthesis constructed in accordance with principles of the present invention is described. Vascular prosthesis 20 comprises helical section 22 and distal anchor section 24, each capable of assuming contracted and deployed states. In FIG. 1, helical section 22 and distal anchor section 24 are each depicted in their respective deployed states.

Vascular prosthesis 20 preferably is formed from a solid tubular member comprising a shape memory material, such as nickel-titanium alloy (commonly known in the art as Nitinol). The solid tubular member then is laser cut, using techniques that are per se known in the art, to a desired deployed configuration, as depicted in FIG. 1A. An appropriate heat treatment, per se known in the art, then may be applied to solid regions 33 of vascular prosthesis 20 while the device is held in the desired deployed configuration (e.g., on a mandrel). The treatment of the shape memory material allows vascular prosthesis 20 to self-deploy to the desired deployed configuration, depicted in FIG. 1, for purposes described hereinafter.

Distal anchor section 24 preferably has a generally zig-zag configuration in the deployed state, as shown in FIG. 1A. The zig-zag configuration preferably is formed by laser cutting a solid tube, as described hereinabove, to form a pattern comprising plurality of struts 31 disposed between plurality of bends 32.

Helical section 22 preferably comprises a helical mesh configuration in the deployed state, as depicted in FIG. 1. The helical mesh configuration includes a plurality of substantially flat turns 26. Plurality of turns 26 may include a multiplicity of openings provided in different shapes and sizes, as illustrated by larger rectangular openings 25, smaller rectangular openings 28 and small circular openings 29. The multiplicity of openings are disposed between solid regions 33 of the shape memory material used to form vascular prosthesis 20. Alternatively, turns 26 may comprise fully covered sections 39, as depicted hereinbelow in FIG. 7C.

As will be apparent to one skilled in the art of stent design, the configuration of helical section 22 depicted herein is merely for illustrative purposes. Any combination of covered sections 39, circular openings 29, large or small rectangular openings, or any other shape may be provided along portions of turns 26, as desired. Plurality of turns 26 similarly may comprise exclusively one type of opening, such as small circular openings 29. Alternatively, plurality of turns 26 may be completely solid, such that the openings are omitted altogether. As will be apparent to those skilled in the art, the combination of solid regions and openings may be provided along the length of helical section 22, for example, to selectively increase surface area and drug delivery capabilities along helical section 22, or to influence flow dynamics within a vessel.

Helical section 22 includes distal turn 34 that transitions into bend 32 of distal anchor section 24, thereby forming junction 23. Proximal turn 35 of helical section 22 forms a free end that permits helical section 22 to conform to a natural configuration of a patient's vessel, as described hereinbelow with respect to FIG. 7.

Figure 2:
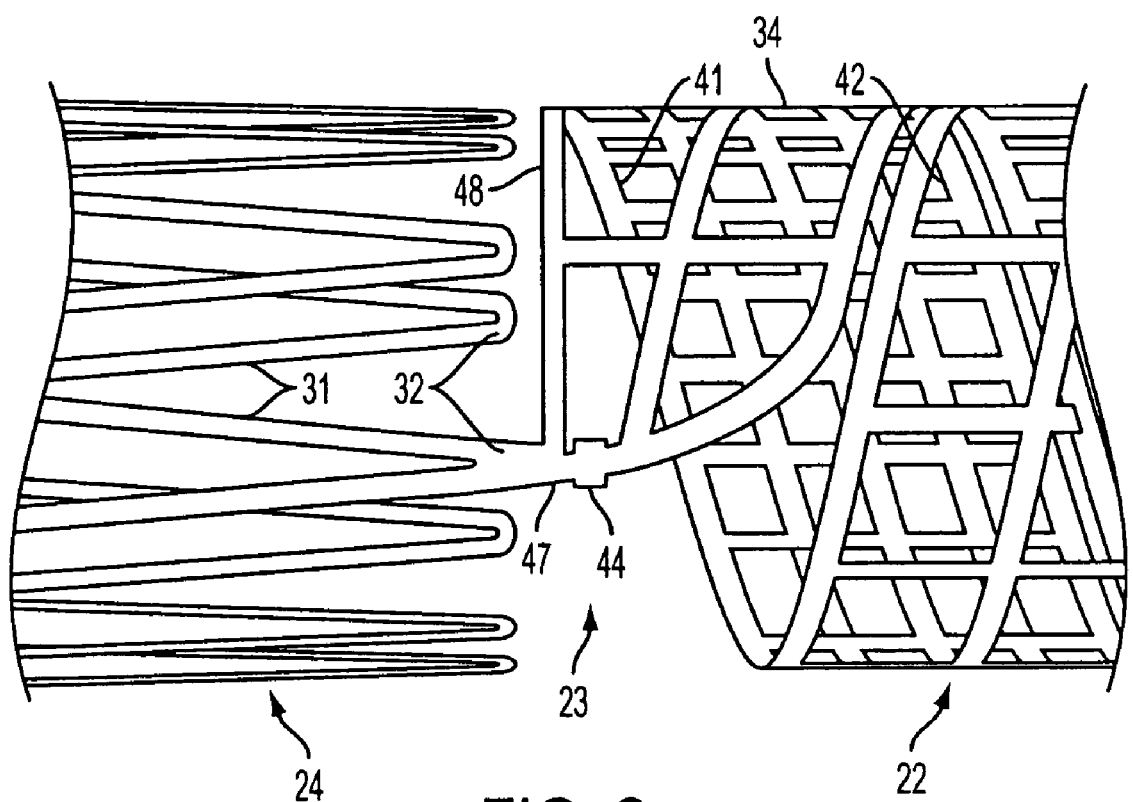
FIG. 2 is a side view describing features of the junction of the prosthesis of FIG. 1.

Referring now to FIG. 2, features of junction 23 of FIG. 1 are described in greater detail. Junction 23 is disposed between helical section 22 and distal anchor section 24 of vascular prosthesis 20. Junction 23 preferably comprises extension strut 47 that is coupled to at least one bend 32 of distal anchor section 24. Junction 23 extends in a proximal direction towards helical section 22 and ultimately transitions into proximal wall 42 of distal turn 34, as shown in FIG. 2.

Junction 23 further preferably comprises substantially orthogonal segment 48, i.e., a segment that is substantially orthogonal to a longitudinal axis of vascular prosthesis 20. Segment 48 transitions into extension strut 47 in the vicinity of bend 32, and further transitions into distal wall 41 of distal turn 34, as shown in FIG. 2.

Junction 23 may comprise one or more radiopaque markers 44, such as a radiopaque marker band or coating. Radiopaque marker 44 facilitates positioning of junction 23 at a desired longitudinal position within a patient's vessel, and further facilitates alignment of vascular prosthesis 20 at a desired radial orientation within the vessel. For example, radiopaque marker 44 may be used to orient helical section 22 so that a desired lateral surface of helical section 22, e.g., comprising covered sections 39 or small circular openings 29, deploys to overlay the arc of a vessel in which an aneurysm is situated.

It will be apparent to those skilled in the art that junction 32 may comprise other strut arrangements to connect distal anchor section 24 to helical section 22. For example, more than one extension strut 47 may be coupled between bends 32 and distal turn 34 of helical section 22. Alternatively, helical section 22 and distal anchor section 24 may be manufactured as two distinct sections, then coupled together to form a junction. In this embodiment, the junction may be formed when distal turn 34 of helical section 22 is coupled to one or more bends 32 situated at proximal end 37 of distal anchor section 24. Distal turn 34 may be coupled to one or more bends 32 using, e.g., a solder, or the sections alternatively may be mechanically coupled together, e.g., using a rivet or other means, as will be apparent to one skilled in the art.

Figure 3:
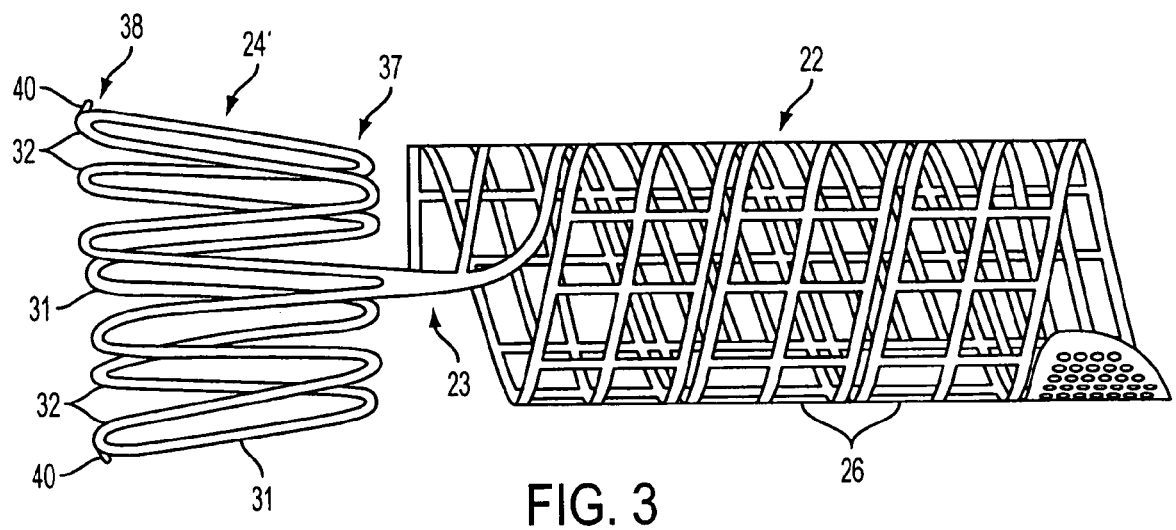
FIG. 3 is a side view of a vascular prosthesis having a distal anchor section that is biased radially outward.

Referring now to FIG. 3, an alternative embodiment of distal anchor section 24 of FIG. 1 is described. In FIG. 3, distal anchor section 24' has proximal end 37 and distal end 38. Distal end 38 is biased radially outward with respect to the longitudinal axis of vascular prosthesis 20. The deployed configuration of distal anchor section 24' may be established by heat treating a shape memory material, using techniques that are per se known in the art, as described above. Distal anchor section 24' is configured to impose an increased radial outward force upon a patient's vessel and may further improve anchoring of the prosthesis within the vessel.

Figure 4:
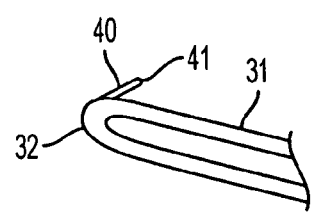
FIG. 4 is an enlarged view of the distal end of the prosthesis of FIG. 3.

Distal end 38 of distal anchor section 24' further may comprise at least one barb 40 protruding from bend 32 and/or a distal portion of strut 31, as depicted in FIG. 4. Barb 40 is configured to extend radially outward and in a proximal direction with respect to a longitudinal axis of vascular prosthesis 20. Each barb 40 may comprise sharpened tip 41, which is configured to engage a patient's vessel when distal anchor section 24' is deployed in a vessel, as described in hereinbelow with respect to FIG. 7.

Figure 5:
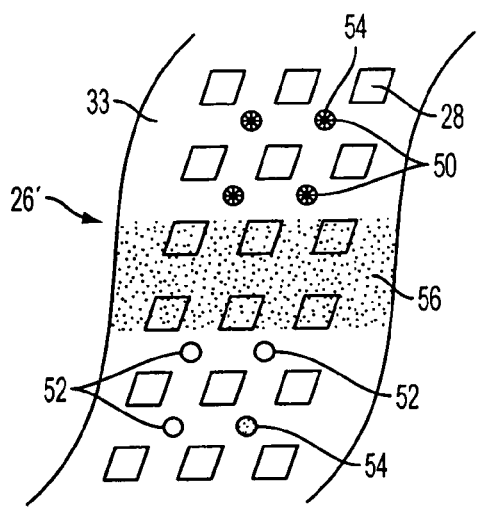
FIG. 5 is a side view illustrating different drug delivery modalities.

Referring now to FIG. 5, different drug delivery modalities that may be used in conjunction with vascular prosthesis 20 of the present invention are described. In FIG. 5, illustrative turn 26' of helical section 22 comprises multiplicity of openings 28 disposed between solid regions 33, and further comprises at least one dimple 50 and/or through hole 52 disposed in solid regions 33. Each dimple 50 and through hole 52 may have therapeutic agent 54 disposed therein. Therapeutic agent 54 may be disposed in the matrix of a bioabsorbable polymer, and the drug may be gradually released into a localized region of an arterial wall. Dimples 50 may be selectively disposed on an interior surface of turn 26', and/or disposed on an exterior surface of turn 26', as depicted in FIG. 5.

One or more turns 26 may be selectively coated with elastomeric polymer 56, such as polyurethane. Elastomeric polymer 56 may partially or fully cover selected regions of turns 26. For example, elastomeric polymer 56 may be disposed on one arc of the circumference of helical section 22 to overlay an aneurysm and reduce blood flow into a sac of the aneurysm. Additionally, therapeutic agent 54 may be disposed on elastomeric polymer 56, which increases the working surface area of helical section 22.

Alternatively, the therapeutic agent may be disposed directly on solid region 33, either with or without the use of elastomeric polymer 56.

Figure 6:
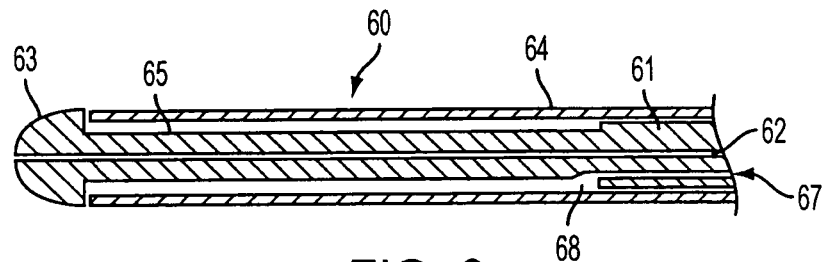
FIG. 6 is a side sectional view of a delivery system that may be used in conjunction with the vascular prosthesis of FIG. 1.

Referring now to FIG. 6, a delivery system suitable for use with the vascular prosthesis of the present invention is described. In FIG. 6, delivery system 60 is similar to that disclosed in U.S. Pat. No. 4,665,918 to Garza et al., and includes catheter 61 having central lumen 62, nose cone 63 and outer sheath 64. Catheter 61 includes recessed portion 65 that cooperates with outer sheath 64 to retain helical section 22 and distal anchor section 24 of vascular prosthesis 20 in their respective contracted states for transluminal delivery.

Delivery system 60 also may comprise fluid delivery lumen 67, which may be used to deliver chilled saline to vascular prosthesis 20 during delivery of the device. Fluid delivery lumen 67 may be disposed within catheter 61, as depicted in FIG. 6, and one or more ports 68 may be formed in a distal lateral surface of catheter 61 to facilitate fluid communication between lumen 67 and recessed portion 65.

Turning now to FIG. 7, a preferred method of using vascular prosthesis 20 of the present invention, for example, in the treatment of an aneurysm, is described. It will be apparent from the method steps described herein that vascular prosthesis 20 also may be used in general stenting procedures, for example, to maintain patency in a vessel after a carotid angioplasty procedure, or may be used as an intravascular drug delivery device, or may be used in other applications apparent to those skilled in the art.

Figure 7A:
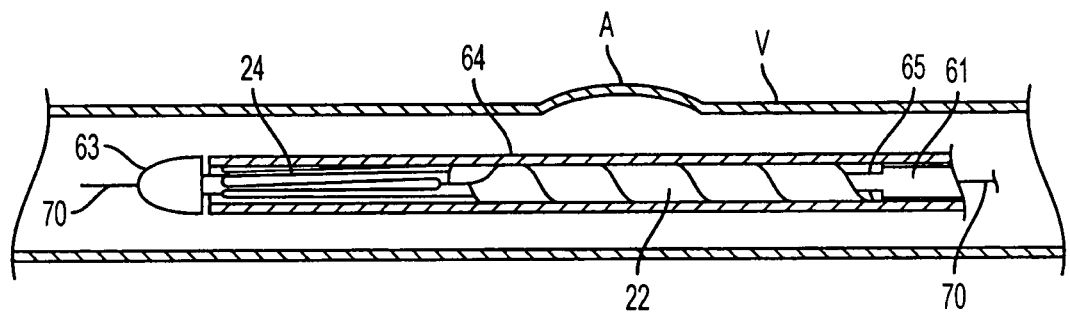
FIGS. 7A-7C are side sectional views illustrating use of the vascular prosthesis of FIG. 1 in the treatment of an aneurysm.

In FIG. 7A, vascular prosthesis 20 of FIG. 1 is provided in the fully contracted state disposed between recessed portion 65 of catheter 61 and outer sheath 64 of FIG. 6. Specifically, distal anchor section 24 is compressed to its contracted delivery state about recessed portion 65 of catheter 61, and the plurality of turns of helical section 22 are wound down to a contracted delivery state about recessed portion 65, as shown in FIG. 7A. Outer sheath 64 is disposed over helical section 22 and distal anchor section 24, as depicted, to retain both sections in their contracted states.

First, guide wire 70 is percutaneously and transluminally advanced through a patient's vasculature, using techniques that are per se known in the art, until a distal end of guide wire 70 is positioned distal of aneurysm A, which is situated in vessel V. Delivery system 60, having vascular prosthesis 20 contracted therein, then is advanced over guide wire 70 via central lumen 62 of catheter 61. Nose cone 63 serves as an atraumatic bumper during advancement of delivery system 60. Delivery system 60 is advanced under fluoroscopic guidance until helical section 22 is situated adjacent aneurysm A, as shown in FIG. 7A.

During advancement of delivery system 60 though a patient's vasculature, chilled saline preferably is delivered to vascular prosthesis 20 via fluid delivery lumen 67 and port 68. The chilled saline may be used to increase or maintain the flexibility of prosthesis 20 to facilitate advancement of delivery system 60 over guide wire 70.

Figure 7B:
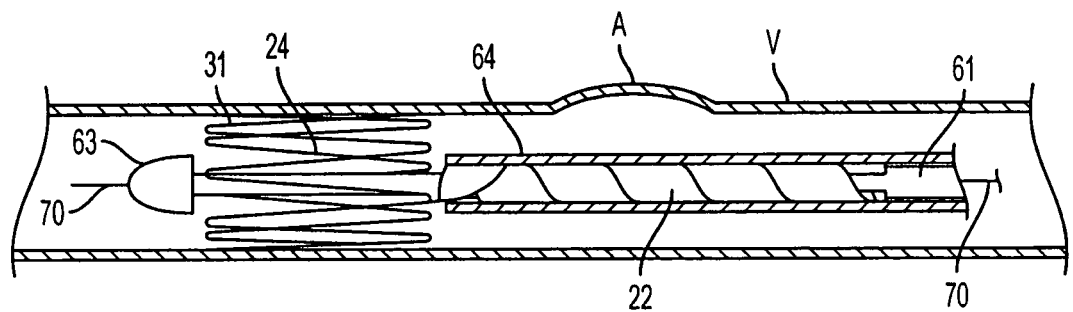

In a next step, outer sheath 64 is retracted proximally to cause distal anchor section 24 to self-deploy distal of aneurysm A, as shown in FIG. 7B. Struts 31 of distal anchor section 24 expand in a radial direction to engage an inner wall of vessel V. Barbs 40 of FIG. 3 may engage vessel V, and/or the distal end of distal anchor section 24 may be biased radially outward with respect to the proximal end (see FIG. 3) to enhance the engagement between distal anchor section 24 and the vessel wall.

Figure 7C:
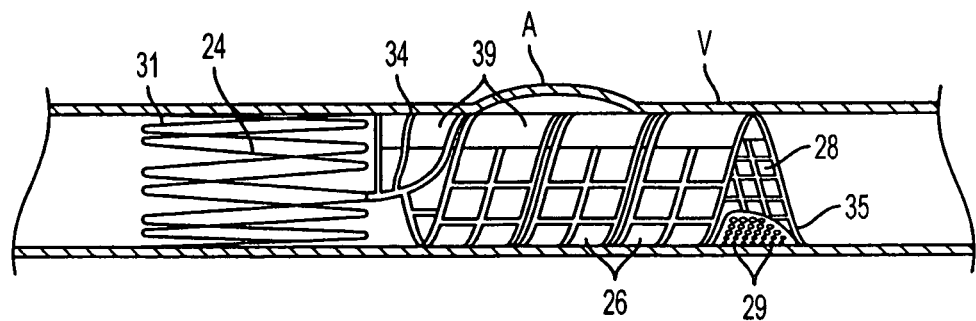

With distal anchor section 24 anchored distal of aneurysm A, outer sheath 64 then is further retracted proximally to cause distal turn 34 of helical section 22 to unwind and deploy to its predetermined shape, as shown in FIG. 7C. As the outer sheath is further retracted, each subsequent turn 26 unwinds one at a time and engages and conforms to an inner wall of vessel V in a controlled manner. When prosthesis system 20 is fully deployed, delivery system 60 then is proximally retracted over guide wire 70 and withdrawn from the patient's vessel, and guide wire 70 is removed.

In accordance with one aspect of the present invention, deploying distal anchor section 24 prior to deploying helical section 22 allows distal anchor section 24 anchors the distal end of the stent to the vessel wall and provides controlled deployment of the helical turns of helical section 22. Advantageously, turns 26 of helical section 22 will be accurately deployed within vessel V, with substantially no proximal or distal shifting with respect to the vessel as outer sheath 64 is retracted.

Moreover, by deploying distal anchor section 24 prior to deploying helical section 22, drawbacks associated with the device described in the above-referenced publication to Rivelli may be overcome. Specifically, without a distal anchoring element, the multiplicity of turns of the stent described in the Rivelli publication may experience a tendency to "bunch up," i.e., overlay one another, as the outer sheath is retracted due to friction between the turns and the outer sheath. By contrast, in the present invention, distal anchor section 24 anchors the distal end of the stent prior to retraction of the outer sheath over the helical section, thus overcoming potential friction and reducing the risk that turns 26 will bunch up.

In accordance with another aspect of the present invention, vascular prosthesis 20 of the present invention is configured to be flexible enough to substantially conform to the shape of vessel V without causing the vessel to remodel. In particular, the zig-zag configuration of distal anchor section 24 and the helical configuration of helical section 22 allow for increased flexibility of prosthesis 20. The pitch associated with plurality of turns 26 may be varied to vary the overall flexibility of helical section 22. A lower pitch, whereby adjacent turns 26 are spaced relatively close together, may be employed to increase flexibility of helical section 22. A lower pitch is desirable, for example, to treat cerebral aneurysms so that turns 26 may conform to the vasculature without causing remodeling of the vessel. Conversely, a higher pitch, whereby adjacent turns 26 are spaced further apart, may be employed to increase the rigidity of helical section 22. Such a design may be desirable for use in maintaining patency in a stenosed vessel by increasing rigidity of helical section 22. As a yet further embodiment, the width of the coil may be tapered, as described in the Rivelli publication.

In accordance with another aspect of the present invention, covered sections 39 may be positioned to overlay aneurysm A to significantly reduce blood flow into aneurysm A. Alternatively, smaller rectangular openings 28 or small circular openings 29 may overlay aneurysm A to reduce blood flow into the sac of the aneurysm. Over time, the intima of vessel V will grow over plurality of turns 26 of helical section 22 to completely exclude the aneurysm A from vessel V.

As noted hereinabove, the configuration of helical section 22 depicted in FIG. 7C is merely for illustrative purposes. Any combination of covered sections 39, circular openings 29, large or small rectangular openings, or any other shape may be provided along turns 26, as desired. Plurality of turns 26 similarly may exclusively comprise one type of opening, e.g., small circular openings 29. Alternatively, plurality of turns 26 may be completely solid such that the openings are omitted altogether.

In accordance with yet another aspect of the present invention, therapeutic agents may be delivered to expedite treatment of the aneurysm or prevent restenosis. As described hereinabove with respect to FIG. 5, therapeutic agent 54 may be delivered to a desired location within vessel V, either using internal or external dimples 50, through holes 52, elastomeric polymer 56 and/or solid regions 33 of one or more turns 26.

Therapeutic agent 54 may include, for example, antiplatelet drugs, anticoagulant drugs, agents used for purposes of providing gene therapy to a target region, or any other agent, and may be tailored for a particular application. Radiopaque markers (not shown) may be selectively disposed on turns 26 in the vicinity of the therapeutic agents to facilitate alignment of the therapeutic agents with a target site of a vessel wall. Advantageously, higher doses of such agents may be provided using vascular prosthesis 20 of the present invention, relative to previously known coils or stents having interconnected struts, due to the increased surface area associated with turns 26.

Figure 8A:
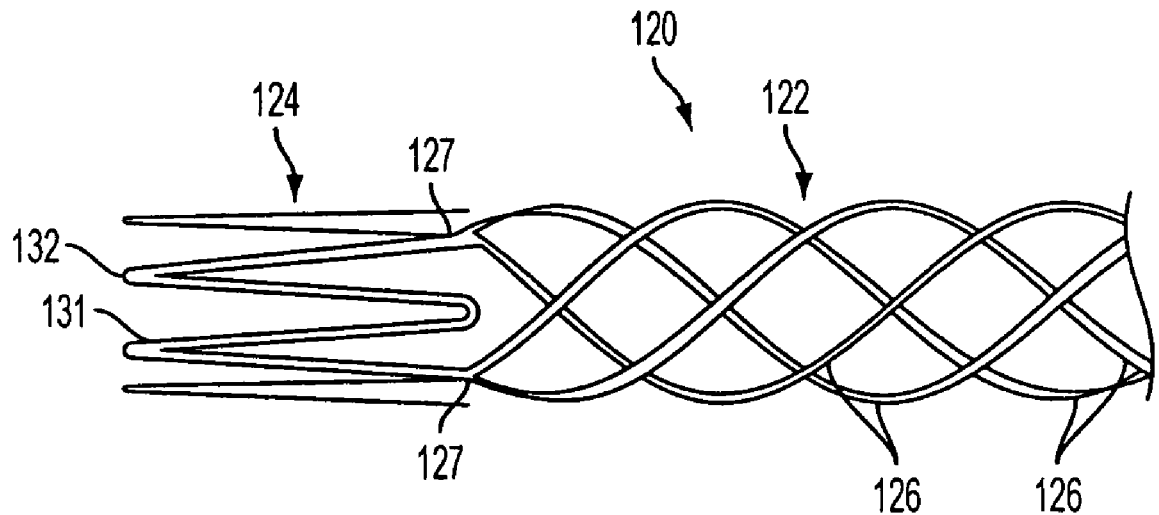
FIGS. 8A-8B are, respectively, side and perspective views of an alternative embodiment of the vascular prosthesis of the present invention.
Figure 8B:
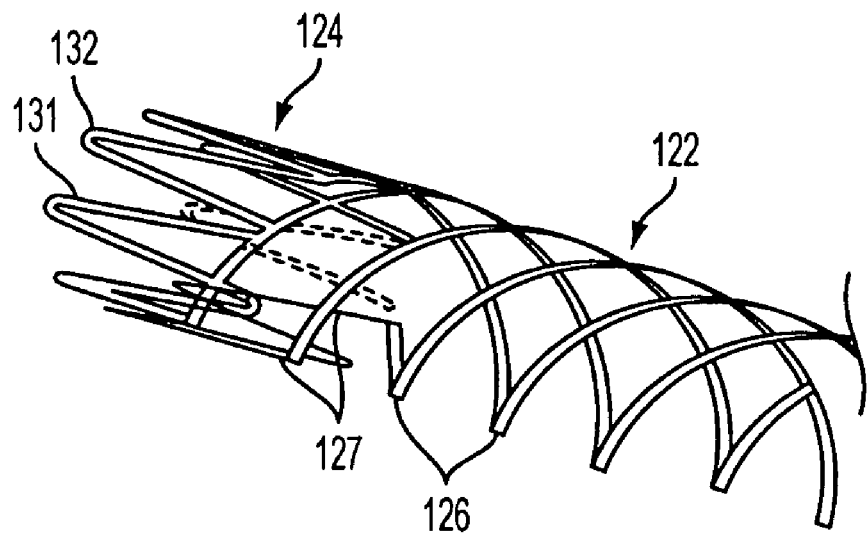

Referring now to FIG. 8, an alternative embodiment of the vascular prosthesis of the present invention is described. Vascular prosthesis 120 comprises helical section 122 and distal anchor section 124. Distal anchor section 124 preferably is provided in accordance with distal anchor section 24 of FIG. 1 and comprises a generally zig-zag configuration including struts 131 and bends 132.

Helical section 122 includes a plurality of individual helical turns 126. Each turn has a distal end that is coupled to a respective bend 132 of distal anchor section 124 at junctions 127, as shown in FIG. 8. Individual helical turns 126 are aligned in a pattern such that each turn maintains its own helical curvature without overlapping with an adjacent turn, as depicted in FIG. 8. Individual helical turns 126 of vascular prosthesis 120 may be heat treated to self-deploy to the configuration shown, and may be wound down to a small diameter in which turns 126 are constrained within delivery system 60 of FIG. 6. The deployment of vascular prosthesis 120 is substantially similar to the deployment of prosthesis 20, as described in detail hereinabove with respect to FIG. 7, and vascular prosthesis 120 encompasses many of the advantages noted hereinabove with respect to vascular prosthesis 20.

Figure 9A:
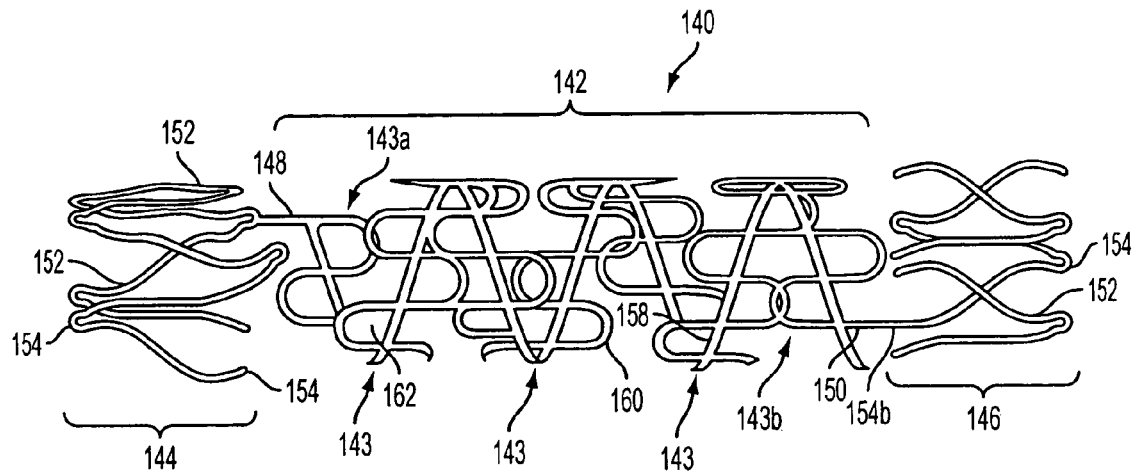
FIGS. 9A-9B are, respectively, side and perspective views of an alternative embodiment of the vascular prosthesis according to the present invention.
Figure 9B:
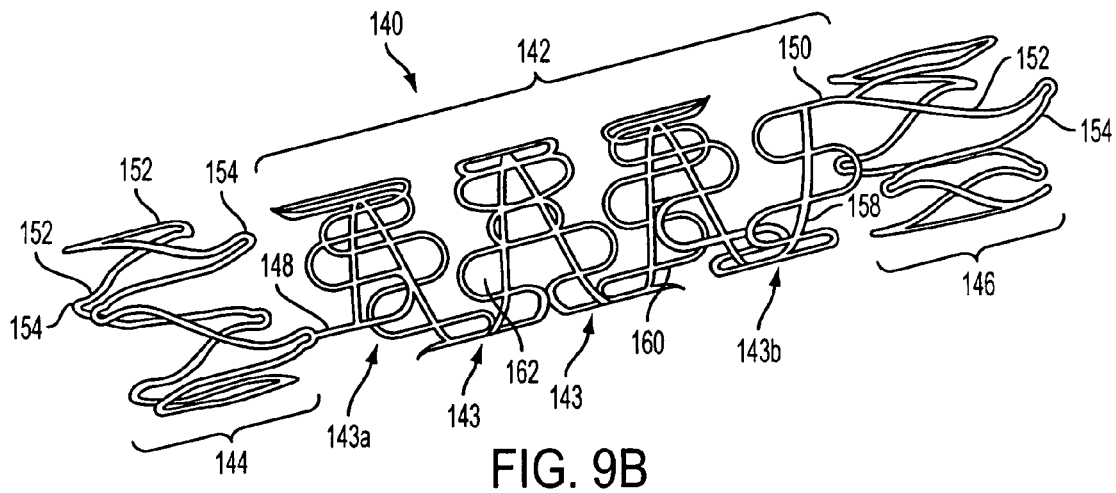

With respect to FIGS. 9A and 9B, an alternative vascular prosthesis 140 of the present invention is described. Vascular prosthesis 140 comprises helical section 142 having a plurality of turns 143, distal anchor section 144 and proximal anchor section 146. Helical section 142 and distal anchor section 144 are joined at junction 148, while helical section 142 and proximal anchor section 146 are joined at junction 150. Each of the helical section, distal anchor section and proximal anchor section are capable of assuming contracted and deployed states, and each are depicted in their respective deployed states in FIGS. 9A and 9B.

In operation, distal anchor section 144 is configured to be initially deployed within a vessel, followed by helical section 142, and then proximal anchor section 146. Deploying distal anchor section 144 first allows the distal anchor section to anchor the distal end of the stent during subsequent deployment helical section 142. Proximal anchor section 146 preferably is disposed to rotate, either freely or manually, within a delivery catheter about a longitudinal axis of the vascular prosthesis during deployment of helical section 142. Distal anchor section 144 balances the torsional force of the helical section, thereby stabilizing the vascular prosthesis. This action is expected to further reduce shifting and foreshortening of the stent with respect to the vessel wall during deployment of helical section 142. Advantageously, the above-identified order of deployment alleviates drawbacks associated with the prior art such as the tendency of the turns of the helical section to "bunch up" during deployment.

The vascular prosthesis, including distal anchor section 144, helical section 142 and proximal anchor section 146, preferably is formed from a solid tubular member comprising a shape memory material, such as Nitinol, processed as described above with respect to the embodiment of FIG. 1. According to some embodiments, helical turns 143 of helical section 142 may be coated with a drug-laden polymer coating or, alternatively, one or more dimples or through-holes may be disposed in a lateral surface of the turns to elute drugs over an extended period of time.

Referring still to FIG. 9, in the deployed state distal and proximal anchor sections 144, 146 have a generally zig-zag configuration comprising plurality of struts 152 disposed between plurality of bends 154. The zig-zag configuration may be formed by laser cutting a solid tube, as described hereinabove, to form the requisite pattern. Of course, as would be understood by those of ordinary skill in the art, distal and proximal anchor sections 144, 146 may have many other configurations without departing from the scope of the present invention.

In the illustrated embodiment, helical section 142 comprises single helical strut 158 having a series of curvilinear extensions 160 formed on alternating sides of the helical strut. Curvilinear extensions 160 form loops that define plurality of openings 162. Helical section 142 alternatively may comprise the helical mesh configuration of FIG. 1 or any other suitable pattern.

With further reference to FIG. 9, helical section 142 has distal turn 143a that transitions into bend 154a of distal anchor section 144, thereby forming junction 148. Likewise, helical section 142 has proximal turn 143b that transitions into bend 154b of proximal anchor section 146, thereby forming junction 150. It will be apparent to those skilled in the art that other strut arrangements may be employed to connect distal and proximal anchor sections 144, 146 to helical section 142. For example, more than one strut may be coupled between helical section 142 and anchor sections 144, 146. Alternatively, helical section 142 and anchor sections 144, 146 may be manufactured as distinct pieces, then coupled together.

Figure 10:
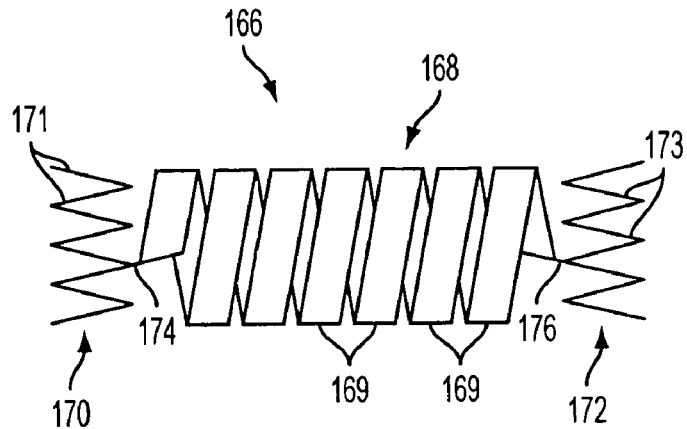
FIG. 10 is a schematic representation of the vascular prosthesis of FIG. 9.

Referring to FIG. 10, vascular prosthesis 166 of the present invention is illustrated schematically as having helical section 168 sandwiched between distal anchor section 170 (having struts 172) and proximal anchor section 172 (having struts 173). Helical section 168 comprises plurality of turns 169. Anchor sections 170, 172 are joined to helical section 168 via junctions 174, 176, respectively. Besides being joined at opposite ends of the helical section, anchor sections 170, 172 are otherwise substantially identical. Similar to previous embodiments, the helical section and anchor sections are capable of assuming contracted and deployed states, and each are depicted in their respective deployed states in FIG. 10.

In the illustrated embodiment, helical section 168 comprises a single helical strut and anchor sections 170, 172 comprise radially expanding members having a generally zig-zag configuration. However, as would be understood by those of ordinary skill in the art, helical section 168 and anchor sections 170, 172 may have many other configurations without departing from the scope of the present invention.

Figure 11:
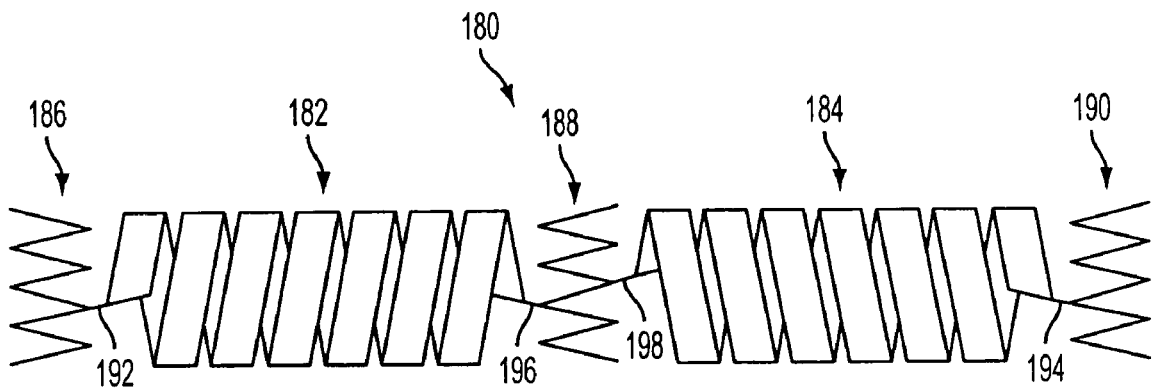
FIG. 11 is a schematic representation of an alternative embodiment of the vascular prosthesis of FIG. 10.

Referring to FIG. 11, vascular prosthesis 180 comprises distal and proximal helical sections 182, 184, and distal, central and proximal anchors sections 186, 188 and 190. In particular, distal anchor section 186 is joined with distal helical section 182 via junction 192 and proximal anchor section 190 is joined with proximal helical section 184 via junction 194. Central anchor section 188 is disposed between the distal and proximal helical sections, and is joined to distal helical section 182 via junction 196 and to proximal helical section 184 via junction 198. Anchor sections 186, 188 and 190 comprise closed bands extending 360° circumferentially. As would be understood by those of ordinary skill in the art, additional helical sections and anchors may be added to the embodiment of FIG. 11 to form a longer vascular prosthesis, without departing from the scope of the present invention.

Figure 12:
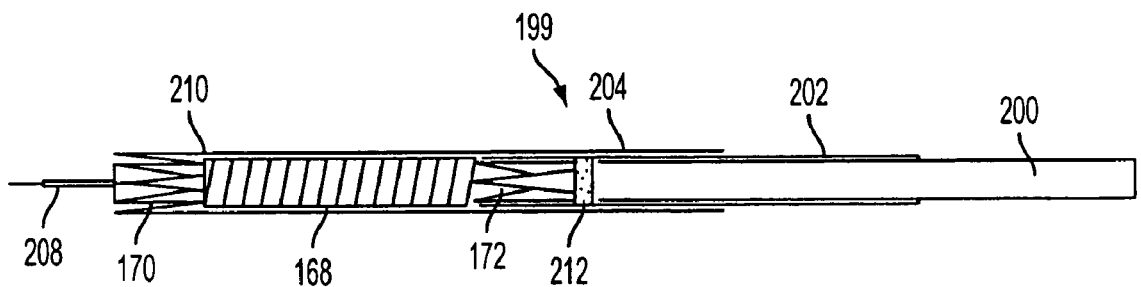
FIG. 12 is a cross-sectional view of a delivery system suitable for use in delivering the vascular prosthesis of FIG. 10.

In FIG. 12, a delivery system suitable for use in delivering a vascular prosthesis of the present invention (e.g., vascular prosthesis 166 of FIG. 10) is described. Delivery system 199 comprises catheter body 200, inner sheath 202, outer sheath 204 and a lumen dimensioned for the passage of guidewire 208. Catheter body 200 preferably includes distal stop 210 at the proximal edge of distal anchor section 170 and proximal stop 212 at the proximal edge of proximal anchor section 172.

Distal stop 210 may comprise a raised ledge on cathether body 200 and include a cut-out so that the proximal ends of struts 171 of distal anchor section 170 (see FIG. 10) bear against the ledge while junction 174 is disposed in the cut-out. Alternatively, distal stop 210 may comprise a plurality of raised pins or knobs that permit junction 174 to pass, but otherwise separate distal anchor section 170 from helical section 168. Proximal stop 212 also may comprise a raised ledge on catheter body 200, and both proximal and distal stops 210 and 212 are radioopaque, so as to be visible under a fluoroscope.

The vascular prosthesis is collapsed onto the catheter body starting with proximal anchor section 172, and inner sheath 202 is advanced distally to capture proximal anchor section 172 in the collapsed configuration around the catheter body. Then, the proximal anchor section is held in a stationary position while helical section 168 is wound around catheter body 200. During this winding process, outer sheath 204 is slowly advanced distally over inner sheath 202 to capture the helical section between catheter body 200 and the outer sheath. Distal anchor section 170 then is collapsed and captured by further advancing outer sheath 204 in the distal direction.

Figure 13A:
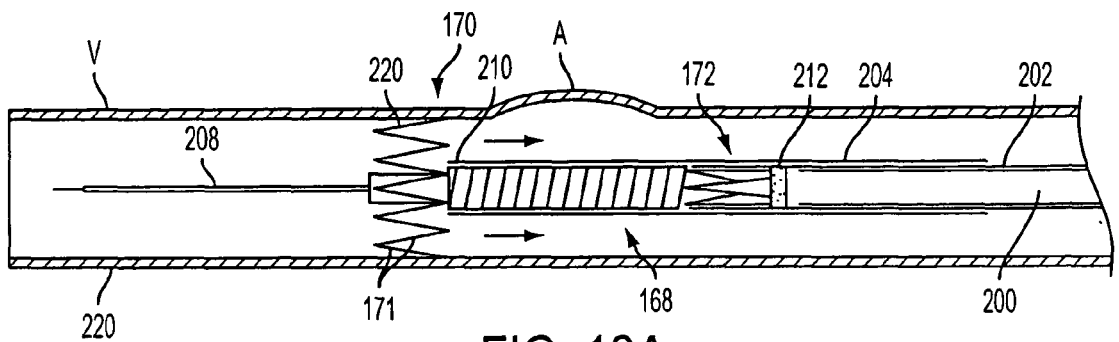
FIGS. 13A-13C are cross-sectional views illustrating delivery of the vascular prosthesis of FIG. 10.

Referring to FIG. 13A, in operation guide wire 208 is percutaneously and transluminally advanced through a patient's vasculature, using techniques that are per se known in the art, until a distal end of guide wire 208 is positioned distal of aneurysm A, which is situated in vessel V. Delivery system 199, having vascular prosthesis 166 contracted therein, then is advanced over guide wire 208 through the central lumen of catheter body 200. Delivery system 199 preferably is advanced under fluoroscopic guidance until helical section 168 is situated adjacent aneurysm A.

Once helical section is positioned adjacent aneurysm A, outer sheath 204 is retracted proximally to cause distal anchor 170 to self-deploy distal of aneurysm A, as shown in FIG. 13A. Proximal movement of outer sheath 204 is halted once the distal edge of outer sheath 204 is substantially aligned with distal stop 210. Struts 171 of distal anchor section 170 expand in a radial direction to engage an inner wall of vessel V. To further enhance engagement between distal anchor section 170 and vessel V, the distal anchor section may be provided with barbs 220, e.g., as described hereinabove with respect to FIGS. 3 and 4.

Figure 13B:
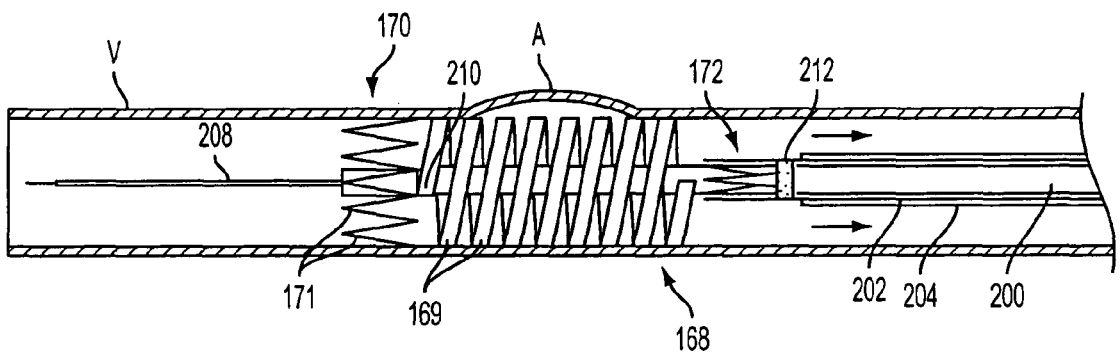

Referring to FIG. 13B, after distal anchor section 170 is secured distal of aneurysm A, outer sheath 204 is further retracted proximally to cause helical section 168 to unwind and deploy to its predetermined shape. During proximal retraction of outer sheath 204, inner sheath 202 is permitted to rotate, or may be manually rotated, to enable helical section 168 to unwind. In the latter case, by controlling the spinning rate of inner sheath 202 as outer sheath 204 is retracted, the clinician may define the spacing between adjacent turns 169 of helical section 168. As the outer sheath is further retracted, each subsequent turn unwinds one at a time and engages and conforms to an inner wall of vessel V in a controlled manner. Proximal movement of outer sheath 204 is again halted once the distal edge of outer sheath 204 is substantially aligned with proximal stop 212.

Figure 13C:
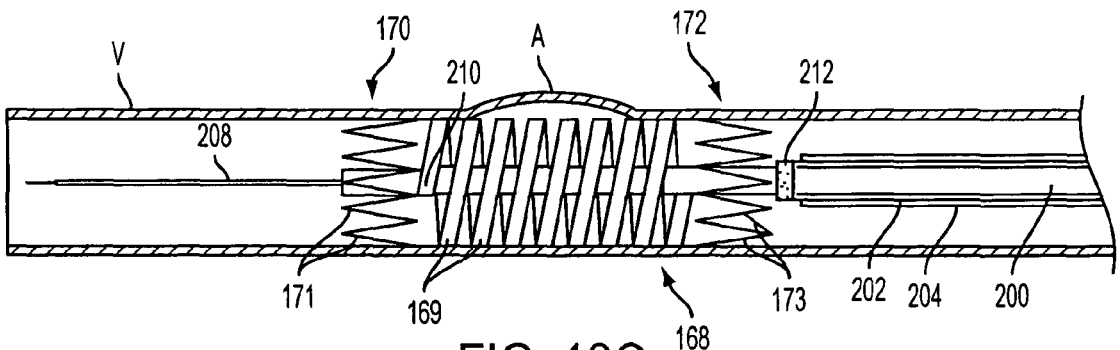

Referring to FIG. 13C, after deployment of helical section 168, inner sheath 202 is retracted proximally to cause proximal anchor 172 to self-deploy proximal of aneurysm A. Struts 173 of proximal anchor 172 expand in a radial direction to engage an inner wall of vessel V. To enhance the engagement between proximal anchor section 172 and vessel V, distal anchor section may be provided with barbs 220, such as described hereinabove. When the vascular prosthesis is fully deployed, delivery system 199 is proximally retracted over guide wire 208 and withdrawn from the patient's vessel, and guide wire 208 is removed.

In accordance with one aspect of the present invention, deploying distal anchor section 170 prior to deploying helical section 168 allows distal anchor section 170 to anchor the distal end of the stent relative to the vessel to provide controlled deployment of the helical turns of helical section 168. Advantageously, turns 169 of helical section 168 will be accurately deployed within vessel V, with substantially no proximal or distal shifting of foreshortening of the stent with respect to the vessel as outer sheath 204 is retracted.

Figure 14A:
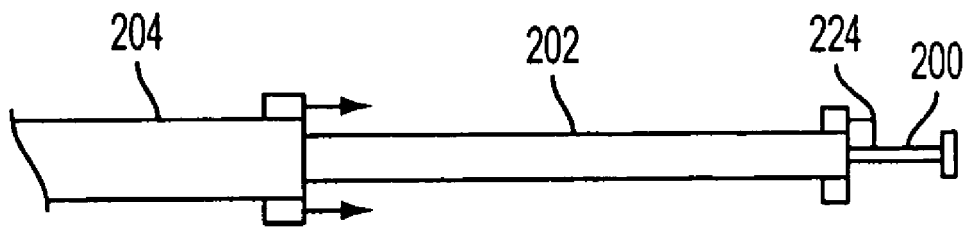
FIGS. 14A-14C are cross-sectional views illustrating the proximal end of the delivery system during delivery of the vascular prosthesis of FIG. 10.
Figure 14B:
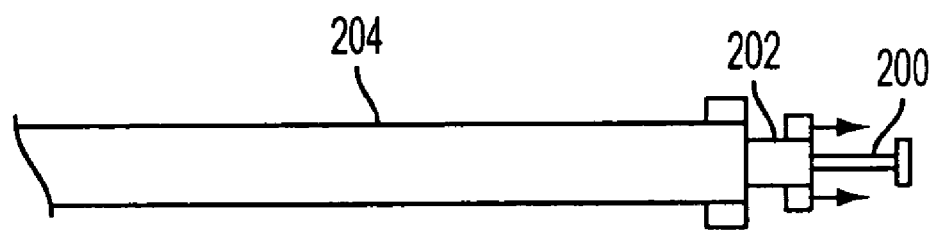
Figure 14C:
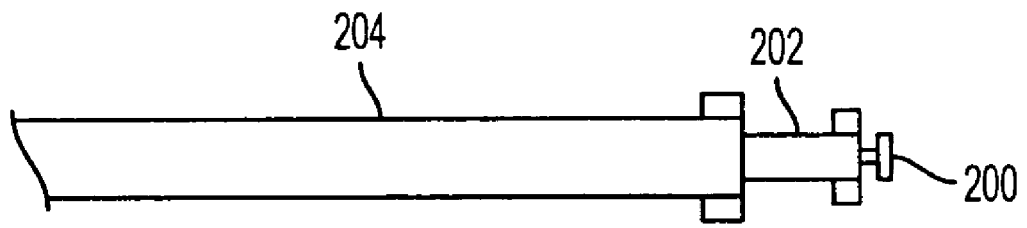

Turning to FIG. 14, a proximal end of the delivery system 199 is described. In FIG. 14A, to deploy the distal anchor section, outer sheath 204 is displaced proximally with respect to inner sheath 202 and catheter body 200. During retraction of outer sheath 204, inner sheath 202 and catheter body 200 preferably are locked together via lock 224. Outer sheath 204 is further displaced proximally with respect to inner sheath 202 and catheter body 200 to deploy helical section 168. As shown in FIGS. 14B and 14C, to deploy proximal anchor section 172, lock 224 is detached and the inner sheath is displaced proximally with respect to catheter body 200.

Figure 15A:
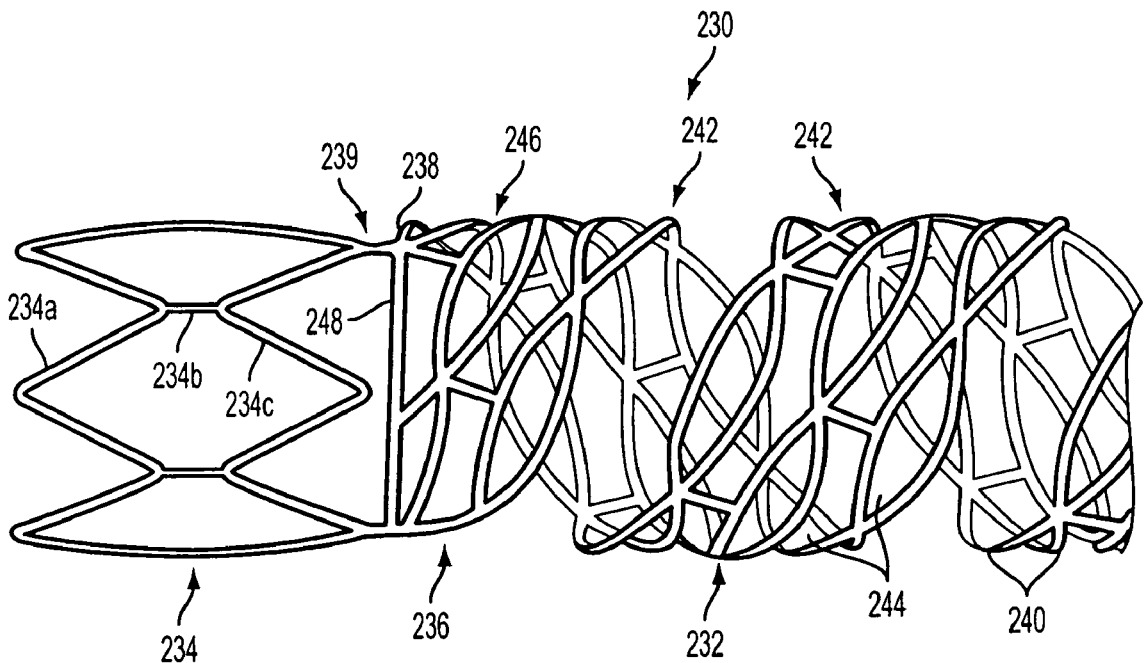
FIGS. 15A-15B are, respectively, side and perspective views of a vascular prosthesis including a torsional stabilizer according to the present invention.
Figure 15B:
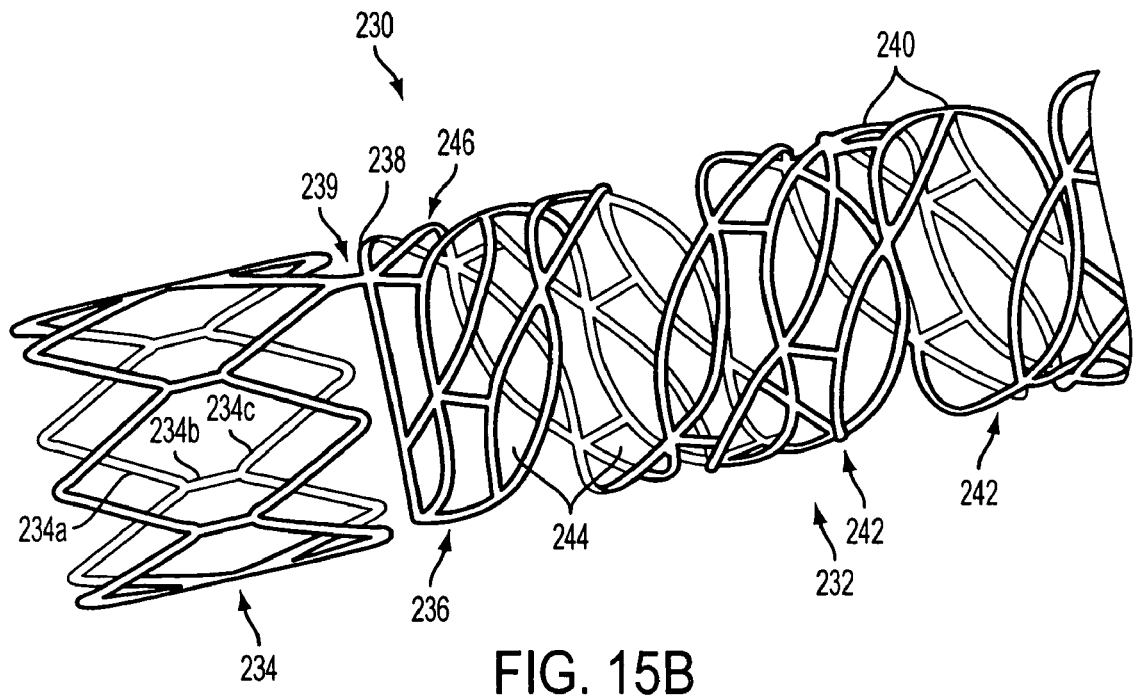

Referring now to FIGS. 15A and 15B, vascular prosthesis 230 including torsional stabilizer 236 according to one aspect of the present invention is described. Vascular prosthesis 230 comprises helical section 232, distal anchor section 234 and torsional stabilizer 236. Helical section 232, distal anchor section 234 and torsional stabilizer 236 are joined at junction 238. Each of the helical section, distal anchor section and torsional stabilizer are capable of assuming contracted and deployed states, and each are depicted in their respective deployed states in FIGS. 15A and 15B.

In operation, distal anchor section 234 is configured to be deployed within a vessel before torsional stabilizer 236, which is configured to be deployed before helical section 232. Deploying distal anchor section 234 first allows the distal anchor section to control subsequent deployment of the helical turns of helical section 232. Torsional stabilizer 236 provides further contact with the vessel wall, thereby providing an additional anchor that transmits torsional forces proximally during deployment of helical section 232. Distal anchor section 234 and torsional stabilizer 236 preferably work in conjunction to balance the torsional force of the helical section and thus stabilize the vascular prosthesis. This action is expected to further reduce shifting and foreshortening of the stent with respect to the vessel wall during deployment of helical section 232. Advantageously, the above-identified order of deployment alleviates drawbacks associated with the prior art such as the tendency of the turns of the helical section to "bunch up" during deployment.

The vascular prosthesis, including distal anchor section 234, helical section 232 and torsional stabilizer 236, preferably is formed from a solid tubular member comprising a shape memory material, such as Nitinol, processed as described hereinabove with respect to the other embodiments. According to some embodiments, torsional stabilizer 236 includes at least one dimple or through-hole disposed on a solid portion of the torsional stabilizer.

Referring still to FIG. 15, in the deployed state distal anchor section 234 has a cell-like configuration comprising pair zig-zags 234a, 234b joined by struts 234c. Alternatively, distal anchor section 234 may include a single zig-zag configuration, such as described with respect to FIG. 1. The cell configuration of FIG. 15 is expected to be more rigid than the single zig-zag configuration, and hence is capable of applying, and withstanding, greater radial force. Either configuration of distal anchor section 234 may be formed by laser cutting a solid tube, as described hereinabove.

Helical section 232 preferably comprises a helical ribbon including plurality of turns 242 having multiplicity of openings 244 provided in varying shapes and sizes. The multiplicity of openings are disposed between solid regions 240 of the shape memory material used to form vascular prosthesis 230. Helical section 232 alternatively may comprise the helical mesh configuration of FIG. 1 or any other suitable pattern. Helical section 232 includes distal turn 246 that transitions into torsional stabilizer 236. Torsional stabilizer 236 comprises strut 248 that preferably remains substantially parallel to distal anchor section 234.

Figure 16:
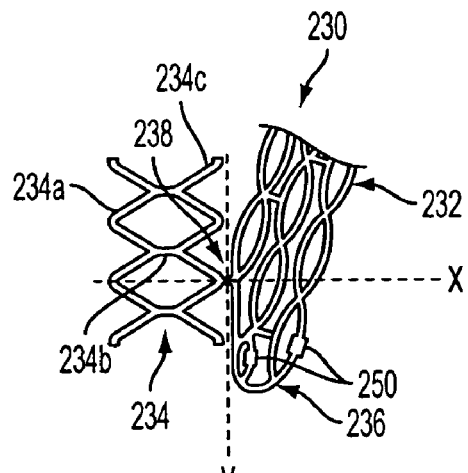
FIG. 16 is a detailed side view of the torsional stabilizer portion of the vascular prosthesis of FIG. 15.

Referring to FIGS. 15 and 16, distal anchor section 234 is coupled to helical section 232 at junction 238. More particularly, strut 234b extends in a proximal direction forming neck 239, which is attached to helical section 232 at junction 238. It will be apparent to those skilled in the art that other strut arrangements may be employed to connect distal anchor section 234 to helical section 232. For example, more than one strut may be coupled between helical section 232 and distal anchor section 234. Alternatively, helical section 232 and distal anchor section 234 may be manufactured as separate pieces, then coupled together.

In FIG. 16, the distal anchor section and helical section are mapped onto an X—Y coordinate system with junction 238 substantially defining an origin (X=0, Y=0). The X-axis is substantially parallel to a longitudinal axis of vascular prosthesis 230 and the Y-axis is substantially orthogonal to the longitudinal axis of vascular prosthesis 230. Torsional stabilizer 236 generally comprises the portion of the helical section that extends past the plane of the X-axis junction 238. According to one aspect of the present invention, torsional stabilizer 236 is an extension of helical section 232 and may comprise a continuation of the helical pattern of the helical section.

Torsional stabilizer 236 optionally may be biased outwardly to provide increased frictional contact with the vessel wall. Torsional stabilizer 236 also may comprise one or more radiopaque markers 250, such as a radiopaque marker band or coating. Radiopaque markers 250 facilitate positioning of torsional stabilizer 236 at a desired longitudinal position within a patient's vessel, and further facilitates alignment of vascular prosthesis 230 at a desired radial orientation within the vessel. For example, radiopaque marker 250 may be used to orient the prosthesis axially within the body vessel.

Figure 17:
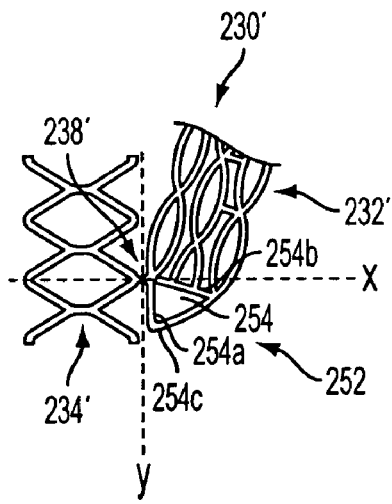
FIG. 17 is a side view of the torsional stabilizer portion of an alternative vascular prosthesis.

In FIG. 17, alternative vascular prosthesis 230' is shown having torsional stabilizer 252 in accordance with the principles of the present invention. Torsional stabilizer 252 comprises loop 254 of material that extends past the plane of the X-axis. Loop 254 is shaped substantially triangularly and includes first segment 254a disposed substantially parallel to the Y-axis, second segment 254b coupled to the helical section, and third segment 254c. As would be appreciated by those of skill in the art, torsional stabilizer 252 may include other shapes and configurations without departing from the scope of the present invention. By way of example, torsional stabilizer 252 may comprise two or more interconnected curvilinear loops.

Figure 18:
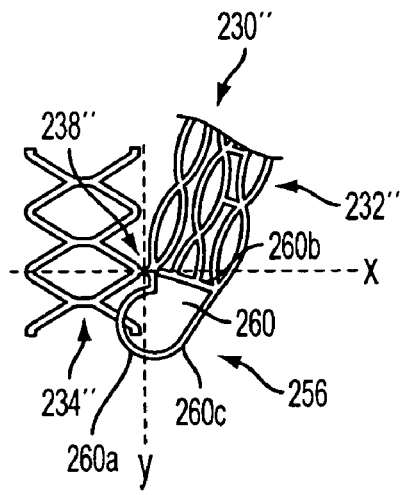
FIG. 18 is a side view of the torsional stabilizer portion of another alternative vascular prosthesis.

In FIG. 18, further alternative vascular prosthesis 230" includes torsional stabilizer 256. Torsional stabilizer 256 comprises loop 260 of material that extends past the plane of both the X-axis and Y-axes, and illustratively includes semicircular portion 260a. Of course, as would be appreciated by those of skill in the art, torsional stabilizer 256 may include other shapes and configurations without departing from the scope of the present invention.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A vascular prosthesis for implantation in a body vessel having a vessel wall, the vascular prosthesis comprising:
   first and second coil-shaped helical elements each having distal and proximal ends;
   the first and second coil shaped helical elements being ribbon type, coil shaped helical elements, each helical element having a width and a thickness with the width being substantially greater than the thickness;

the first coil-shaped helical element extending more than 360° about a longitudinal axis of the prosthesis;

the second coil-shaped helical element extending more than 360° about the longitudinal axis of the prostheses, the second coil-shaped helical element having an opposite direction of rotation to that of the first coil-shaped helical element;

the first and second coil-shaped helical elements arranged in series with the entire first coil-shaped helical element being proximal of the second coil-shaped helical element and with the distal end of the first coil-shaped helical element secured to the proximal end of the second coil-shaped helical element; and an anchor section securing the distal end of the first coil-shaped helical element to the proximal end of the second coil-shaped helical element, the anchor section comprising a closed band extending 360° circumferentially.

2. The vascular prosthesis of claim 1, wherein:

the first and second coil-shaped helical elements are self expanding to engage the vessel wall in an expanded state.

3. The vascular prosthesis of claim 1, wherein:

the first and second coil-shaped helical elements are unwindingly self-expanding helical elements to engage the vessel wall in an expanded state.

4. The vascular prosthesis of claim 1, further comprising more than two coil-shaped helical elements arranged in series.

5. The vascular prosthesis of claim 1, wherein the first coil-shaped helical element and second coil-shaped helical element have equal lengths.

6. The vascular prosthesis of claim 1, wherein each of said first and second coil-shaped helical elements comprises a single length of material.

7. The vascular prosthesis of claim 1, wherein the anchor section comprises a radially self-expanding anchor section.

8. The vascular prosthesis of claim 1, wherein the first and second coil-shaped helical elements are configured in a contracted state suitable for transluminal insertion into the body vessel, the first and second coil-shaped helical elements being capable of expanding to engage the vessel wall.

9. The vascular prosthesis of claim 1, further comprising a radially self-expanding anchor section joined to an end of a coil-shaped helical element.

10. The vascular prosthesis of claim 9, wherein the anchor section is configured to engage the vessel wall to retain the vascular prosthesis in position during deployment of the coil-shaped helical elements.

11. The vascular prosthesis of claim 9, wherein the coil-shaped helical elements and the anchor section each comprise a shape memory material.

12. The vascular prosthesis of claim 11, wherein the shape memory material is a nickel titanium alloy.

13. The vascular prosthesis of claim 9, wherein the coil-shaped helical elements and the anchor section are made separately and then coupled together.

14. The vascular prosthesis of claim 1, further comprising a distal, radially self-expanding anchor section joined to the distal end of the second coil-shaped helical element.

15. The vascular prosthesis of claim 14, wherein the distal anchor section is configured to be deployed within the body vessel before the coil-shaped helical elements are deployed.

16. The vascular prosthesis of claim 14, further comprising a proximal, radially self-expanding anchor section joined to the proximal end of the first coil-shaped helical element.

17. The vascular prosthesis of claim 16, wherein the anchor sections each comprise a plurality of elongated elements having a generally zig-zag configuration.

* * * * *